(12) United States Patent
Starr et al.

(10) Patent No.: US 11,868,370 B2
(45) Date of Patent: *Jan. 9, 2024

(54) SYSTEM AND METHOD FOR MERGING SLOWLY CHANGING DATA

(71) Applicant: IQVIA Inc., Parsippany, NJ (US)

(72) Inventors: Thomas Starr, Danbury, CT (US); Ivan Gudzei, Danbury, CT (US); Dave Musgrove, Danbury, CT (US); Katarzyna Jurkiewicz, Danbury, CT (US); Sergey Sinkevich, Danbury, CT (US); Vladimir Karaychentsev, Danbury, CT (US)

(73) Assignee: IQVIA Inc., Parsippany, NJ (US)

( * ) Notice: Subject to any disclaimer, the term of this patent is extended or adjusted under 35 U.S.C. 154(b) by 81 days.

This patent is subject to a terminal disclaimer.

(21) Appl. No.: 17/717,246

(22) Filed: Apr. 11, 2022

(65) Prior Publication Data

US 2022/0237207 A1 Jul. 28, 2022

Related U.S. Application Data

(63) Continuation of application No. 17/027,044, filed on Sep. 21, 2020, now Pat. No. 11,321,355, which is a continuation of application No. 15/858,160, filed on Dec. 29, 2017, now Pat. No. 10,795,915.

(51) Int. Cl.
| | |
|---|---|
| *G06F 16/27* | (2019.01) |
| *G06F 16/11* | (2019.01) |
| *H04L 67/1097* | (2022.01) |
| *G06F 16/23* | (2019.01) |

(52) U.S. Cl.
CPC .......... *G06F 16/275* (2019.01); *G06F 16/119* (2019.01); *G06F 16/23* (2019.01); *H04L 67/1097* (2013.01)

(58) Field of Classification Search
None
See application file for complete search history.

(56) References Cited

U.S. PATENT DOCUMENTS

| | | |
|---|---|---|
| 9,836,229 B2 | 12/2017 | D'Sa et al. |
| 11,016,954 B1 | 5/2021 | Babocichin et al. |
| 11,321,355 B2 | 5/2022 | Starr et al. |
| 2006/0294151 A1 | 12/2006 | Wong et al. |
| 2009/0094258 A1 | 4/2009 | Chen et al. |

(Continued)

*Primary Examiner* — Eddy Cheung
(74) *Attorney, Agent, or Firm* — Fish & Richardson P.C.

(57) ABSTRACT

The disclosure generally describes computer-implemented methods, software, and systems for accessing volumes of data records structured to include sets dimensions, each dimension labelled in a manner specific to respective entities; identifying candidates data records keyed by managed keys that span a subset of dimensions even though at least one dimension from the subset of dimensions is labelled differently between the different volumes; comparing the candidate data records from the different volumes to determine whether a particular managed key is valid based on contents of the candidate data records from the different volumes; in response to determining that the particular managed key is valid, combining the candidate data records keyed by the valid managed key to be merged and accessible as one continuous entry; and in response to determining that the particular managed key is invalid, combining the candidate data records from the different volumes as separate entries.

18 Claims, 4 Drawing Sheets

(56) References Cited

U.S. PATENT DOCUMENTS

| | | |
|---|---|---|
| 2009/0177647 A1 | 7/2009 | Oliver et al. |
| 2011/0231454 A1 | 9/2011 | Mack |
| 2013/0198129 A1 | 8/2013 | Gorman et al. |
| 2014/0114926 A1 | 4/2014 | Anderson |
| 2015/0254308 A1 | 9/2015 | Scott et al. |
| 2016/0139838 A1 | 5/2016 | D'Sa et al. |
| 2017/0315728 A1 | 11/2017 | Zheng et al. |
| 2017/0315740 A1 | 11/2017 | Corsi et al. |
| 2018/0165287 A1 | 6/2018 | Lu et al. |
| 2018/0183774 A1 | 6/2018 | Campagna et al. |
| 2021/0004388 A1 | 1/2021 | Starr et al. |

| PANEL DSCR 302 | MANUFACTURER DSCR 304 | LOCAL PRODUCT DSCR 306 | PACK DSCR 308 | |
|---|---|---|---|---|
| US FOODSTORES | HOSPIRA | MAGNESIUM SULF | IVPB 4G /ML 24 100ML | 318 |
| US FOODSTORES | HOSPIRA | MAGNESIUM SULF | IVPB 4G /100 24 100ML | |
| US FOODSTORES | HOSPIRA | MAGNESIUM SULF | IVPB 4G /100 24 100ML | |
| US FOODSTORES | PFIZER 314 | MAGNESIUM SULF | IVPB 4G /100 24 100ML | |
| | | | | |
| BELGIUM HOSPITAL | WARNER CHILCOTT 324A | CACIT | VIT D3 1/880 8G | |
| BELGIUM HOSPITAL | TEVA PHARM.BELGIUM | CACIT | VIT D3 1/880 8G | |
| BELGIUM HOSPITAL | TEVA PHARM.BELGIUM | CACIT | VIT D3 1/880 8G | |
| BELGIUM HOSPITAL | VEMEDIA CONS.HEALT 324B | CACIT | VIT D3 1/880 8G | |
| BELGIUM HOSPITAL | VEMEDIA CONS.HEALT | CACIT | VIT D3 1/880 8G | |
| BELGIUM HOSPITAL | TEVA PHARM.BELGIUM 324C | CACIT | VIT D3 1/880 8G | |
| | | | | |
| PORTUGAL RETAIL | PENTAFARMA | COTIASAR MG | CPR REV 50MG 10 LO+H | 328 |
| PORTUGAL RETAIL | PENTAFARMA | COTIASAR MG | CPR REV 50/ 12.5MG 10 LOSA | |
| PORTUGAL RETAIL | PENTAFARMA | COTIASAR MG | CPR REV 50/ 12.5MG 10 LOSA | |
| PORTUGAL RETAIL | TECNIGEN 334 | COTIASAR MG | CPR REV 50/ 12.5MG 10 LOSA | |
| | | | | |
| US DRUGSTORES | HOSPIRA | DOPAMINE/D5W | LF/CR 200MG/250 12 250ML | 338 |
| US DRUGSTORES | HOSPIRA | DOPAMINE/D5W | BAG 200MG/250 12 250ML | |
| US DRUGSTORES | HOSPIRA 344 | DOPAMINE/D5W | BAG 200MG/250 12 250ML | |
| US DRUGSTORES | PFIZER 354 | DOPAMINE/D5W | BAG 200MG/250 12 250ML | |
| | | | | |
| FRANCE RETAIL | PROSTRAKAN | PECFENT | PULV NAS 8D 400Y /DOS | |
| FRANCE RETAIL | KYOWA KIRIN | PECFENT | PULV NAS 8D 400Y /DOS | |
| FRANCE RETAIL | KYOWA KIRIN | PECFENT | PULV NAS 8D 400Y /DOS | |
| FRANCE RETAIL | KYOWA KIRIN | PECFENT | PULV NAS 8D 400Y /DOS 1.55ML | 348 |

FIG. 3

SYSTEM AND METHOD FOR MERGING SLOWLY CHANGING DATA

CROSS-REFERENCE TO RELATED APPLICATIONS

This application is a continuation of U.S. application Ser. No. 17/027,044 filed Sep. 21, 2020, which is a continuation of U.S. application Ser. No. 15/858,160 filed Dec. 29, 2017 the entire contents of which are hereby incorporated by reference in its entirety.

BACKGROUND

Database information may be stored in a distributed manner.

TECHNICAL FIELD

Database information in distributed storage are managed to maintain data consistency.

SUMMARY

In one aspect, some implementations provide a computer-implemented method for merging data records from at least two different entities, the method comprising: accessing a first volume of data records from a first data server managed by a first entity, the first volume structured to include a first set of dimensions, each dimension labelled in a manner specific to the first entity; accessing a second volume of data records from a second data server managed by a second entity that is different from the first entity, the second volume structured to include a second set of dimensions, each dimension labelled in a manner specific to the second entity; identifying candidates data records keyed by managed keys that span a subset of dimensions included by the first volume and the second volume even though at least one dimension from the subset of dimensions is labelled differently between the first volume and the second volume; comparing the candidate data records from the first volume with the candidate data records from the second volume to determine whether a particular managed key is valid based on contents of the candidate data records from the first and second volumes; in response to determining that the particular managed key is valid, consolidating the first volume with the second volume by joining the candidate data records from the first volume with the candidate data records from the second volume according to the valid managed key such that the candidate data records from the first and second volumes keyed by the valid managed key are merged and accessible as one continuous entry; and in response to determining that the particular managed key is invalid, consolidating the first volume with the second volume by combining the candidate data records from the first volume and the candidate data records from the second volume keyed by the particular managed key as separate entries.

Implementations may include one or more of the following features. In one configuration, comparing the candidate data records from the first volume with the candidate data records from the second volume to determine whether a particular managed key is valid may include: comparing the contents of the candidate data records from the first volume keyed by the particular managed key with the contents of the candidate data records from the second volume keyed by the specific managed key.

Comparing the candidate data records from the first volume with the candidate data records from the second volume to determine whether a particular managed key is valid may include: comparing the contents of candidate data records from the first and second volumes that cover more than a threshold duration that is contemporaneous in nature, the contents of data records keyed by the particular managed key.

Comparing the candidate data records from the first volume with the candidate data records from the second volume may utilize a fuzzy logic to determine whether the particular managed key is valid. The method may further include: comparing the contents of the candidate data records from the first volume with the contents of the candidate data records from the second volume to determine whether the contents of the candidate data records from the first and second volume substantially match, even though the at least one dimension is labelled differently.

The contents of candidate data records from the first and second volume may substantially match when the candidate data records from the first and second volume are identical for more than a threshold percentage of a duration of the comparison. The contents of candidate data records from the first and second volume may substantially match when the candidate data records from the first and second volume are textually more than a threshold percent identical.

The method may further include scoring a similarity between the contents of candidate data records from the first volume with the contents of the candidate data records from the second volume, wherein the contents of candidate data records from the first and second volume substantially match when the scored similarity exceeds a threshold value.

The method may further include: accessing a third volume of data records from a third data server managed by a third entity that is different from the first and second entities, the third volume structured to include a third set of dimensions, each dimension labelled in a manner specific to the third entity; generating candidates data records under managed keys that span a subset of dimensions included by the consolidated volume and the third volume even though at least one dimension from the subset of dimensions is labelled differently between the consolidated volume and the third volume; comparing the consolidated volume with the third volume to determine whether the particular managed key is valid based on contents of the candidate data records from the consolidated volume and the third volume; in response to determining that the particular managed key is valid, consolidating the consolidated volume with the third volume by combining data records from the consolidated volume with data records from the third volume according to the valid managed key such that the candidate data records from the consolidated and third volumes keyed by the valid managed key are merged and accessible as one continuous entry; and in response to determining that the particular managed key is invalid, consolidating the consolidated volume with the third volume by combining data records from the consolidated volume with data records from the third volume keyed by the particular managed key as separate entries.

The subset of dimensions may further includes three or more dimensions.

In another aspect, implementations include a computer system comprising one or more processors that are configured to perform the operations of: accessing a first volume of data records from a first data server that is different from the computer system and managed by a first entity, the first volume structured to include a first set of dimensions, each dimension labelled in a manner specific to the first entity; accessing a second volume of data records from a second data server that is different from the computer system and managed by a second entity that is different from the first entity, the second volume structured to include a second set of dimensions, each dimension labelled in a manner specific to the second entity; identifying candidates data records keyed by managed keys that span a subset of dimensions included by the first volume and the second volume even though at least one dimension from the subset of dimensions is labelled differently between the first volume and the second volume; comparing the candidate data records from the first volume with the candidate data records from the second volume to determine whether a particular managed key is valid based on contents of the candidate data records from the first and second volumes; in response to determining that the particular managed key is valid, consolidating the first volume with the second volume by joining the candidate data records from the first volume with the candidate data records from the second volume according to the valid managed key such that the candidate data records from the first and second volumes keyed by the valid managed key are merged and accessible as one continuous entry; and in response to determining that the particular managed key is invalid, consolidating the first volume with the second volume by combining the candidate data records from the first volume and the candidate data records from the second volume keyed by the particular managed key as separate entries.

Implementations may include one or more of the following features.

Comparing the candidate data records from the first volume with the candidate data records from the second volume to determine whether a particular managed key is valid may include: comparing the contents of the candidate data records from the first volume keyed by the particular managed key with the contents of the candidate data records from the second volume keyed by the specific managed key.

Comparing the candidate data records from the first volume with the candidate data records from the second volume to determine whether a particular managed key is valid may include: comparing the contents of candidate data records from the first and second volumes that cover more than a threshold duration that is contemporaneous in nature, the contents of data records keyed by the particular managed key.

Comparing the candidate data records from the first volume with the candidate data records from the second volume may utilize a fuzzy logic to determine whether the particular managed key is valid.

The operations may further include: comparing the contents of the candidate data records from the first volume with the contents of the candidate data records from the second volume to determine whether the contents of the candidate data records from the first and second volume substantially match, even though the at least one dimension is labelled differently.

The contents of candidate data records from the first and second volume may substantially match when the candidate data records from the first and second volume are identical for more than a threshold percentage of a duration of the comparison.

The contents of candidate data records from the first and second volume may substantially match when the candidate data records from the first and second volume are textually more than a threshold percent identical.

The operations may further include: scoring a similarity between the contents of candidate data records from the first volume with the contents of the candidate data records from the second volume, wherein the contents of candidate data records from the first and second volume substantially match when the scored similarity exceeds a threshold value.

The operations may further include: accessing a third volume of data records from a third data server that is different from the computer system and managed by a third entity that is different from the first and second entities, the third volume structured to include a third set of dimensions, each dimension labelled in a manner specific to the third entity; generating candidates data records under managed keys that span a subset of dimensions included by the consolidated volume and the third volume even though at least one dimension from the subset of dimensions is labelled differently between the consolidated volume and the third volume; comparing the consolidated volume with the third volume to determine whether the particular managed key is valid based on contents of the candidate data records from the consolidated volume and the third volume; in response to determining that the particular managed key is valid, consolidating the consolidated volume with the third volume by combining data records from the consolidated volume with data records from the third volume according to the valid managed key such that the candidate data records from the consolidated and third volumes keyed by the valid managed key are merged and accessible as one continuous entry; and in response to determining that the particular managed key is invalid, consolidating the consolidated volume with the third volume by combining data records from the consolidated volume with data records from the third volume keyed by the particular managed key as separate entries. The subset of dimensions may include three or more dimensions.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 3 illustrates examples of identifying managed keys.

DETAILED DESCRIPTION

This disclosure generally describes systems and methods for merging voluminous data records from distributed storage that carries slowly changing information. In the healthcare system, for example, large volumes of data records documenting transactional usage of pharmaceutical products are maintained at a variety of locations, each with its own data storage servers. The data records for one particular pharmaceutical product may be labelled in a manner unique to the custodian of the information, as well as in accordance with conventions at the time when such data records are generated. When data records from these diverse database are reconciled, entries that correspond to the same pharmaceutical product may not be linked by virtue of a unique and constant reference indexing key. Some implementations disclosed herein may automatically identify the same records of data in the data warehouse by calculating a probability of match based on comparing the actual contents of the data records and in accordance with a set of rules. In these implementations, only records above a threshold probability of matching can be merged as one contiguous record. For those records that fall under a threshold of matching probability, these records will be added as separate and different entries. These entries can also be reviewed by a human data analyst. The threshold probability of matching can be adjusted for each automatic update, depending on a variety of factors (e.g., client need, or criticality). Such refinement may avoid gaps in data trend when data items changes its attributes (dimensions) slowly, for example, at distributed data warehouses. In response to the determination, contents of the data records may be maintained for consistency, for example, at a primary data server. In some cases, the manner in which data records are labeled at the distributed data warehouses may also be updated. Such update may take the form of synchronization between distributed data warehouses and the primary data server.

Figure 1:
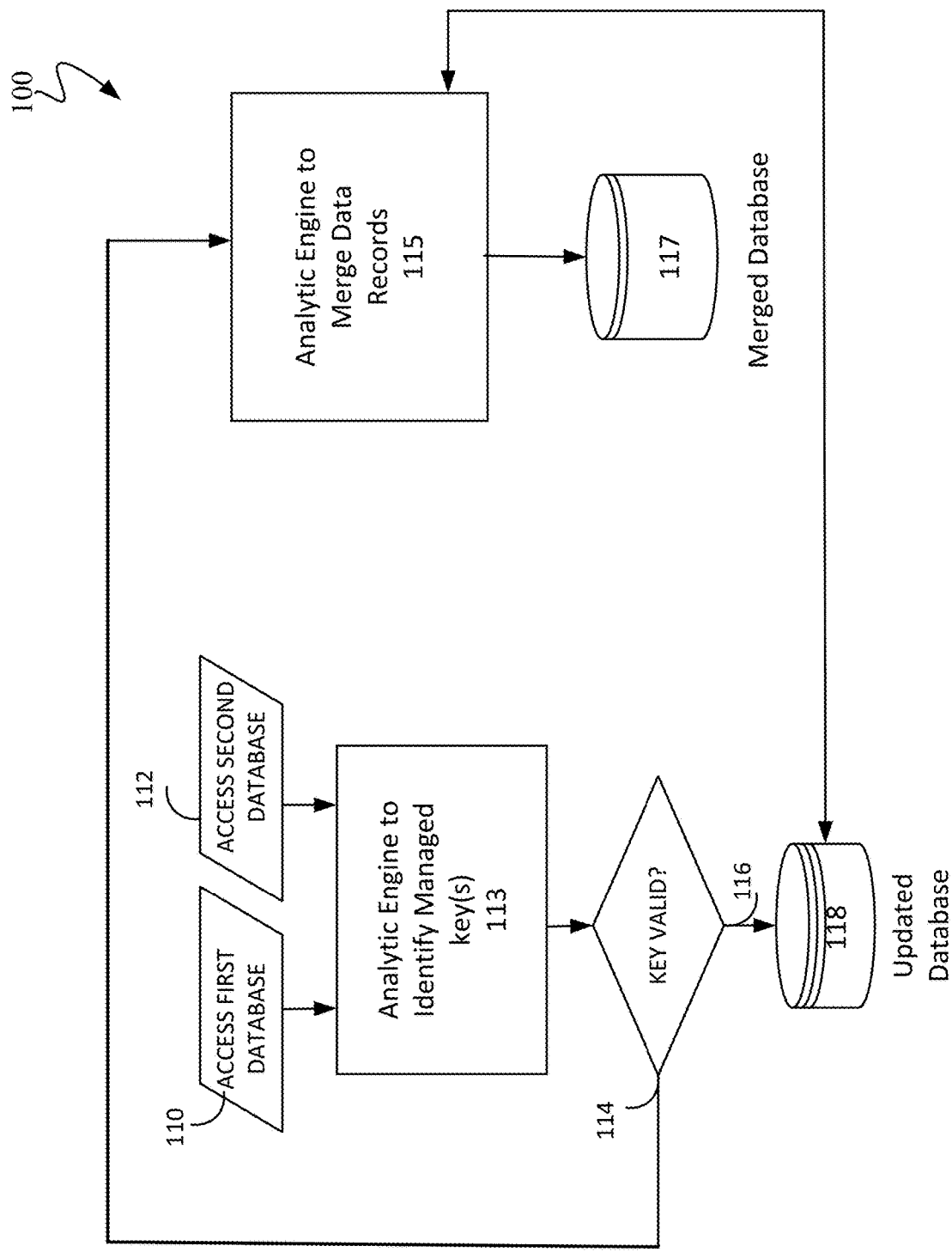
FIG. 1 shows an example of a network configuration to handle distributed databases with slowly changing dimensions.

Referring to FIG. 1, an example of a network configuration 100 is presented. This network configuration is capable of handling distributed databases with slowing changing dimensions (SCD). For context, data warehouse design presumes that data records, such as customer orders, order fulfillment, or product shipments, will accumulate quickly. Yet, the supporting dimension attributes of the data records, such as customer name, product name, product description, or product size, are relatively static. Still, most dimensions are subject to change, albeit slowly (for example, gradually and with passage of time rather than changing on regular schedule, time-base). In Data warehouse applications, the ability to track changes in dimension attributes would be advantageous in order to report historical data. In other words, tracking SCD should enable users assigning proper attribute value to each dimension for given dates. As an illustration, a table with a million rows and many attributes may require historical and current tracking because these attributes are not static; and as such, voluminous data records stored at distributed data warehouses may differ slightly in some of these attributes. Without realizing the slight variations can be ignored, data records referring to the same fact may be kept as separate entries, thereby masking commonality that would otherwise reveal useful insight on trend of the underlying data records.

As illustrated in network configuration 100, data records at a first database may be accessed (110) when communication is established with the first database. Likewise, data records at a first database may be accessed (110) when communication is established with the first database. A database refers to an organized collection of data. A database may include a relational database which may include a collection of schemas, tables, queries, reports, views, and other elements. A database may be configured to have the underlying data model aspects of reality in a manner that supports processes requiring information, such as (for example) modelling the transaction of the distribution and consumption of pharmaceutical products. Within the confines of this disclosure, the various databases may house data records documenting the order, fulfillment, shipping, and reimbursement of consuming pharmaceutical products. In this illustration, a primary data server may establish communication with the first and second databases that are maintained, for example, by separate entities. The communication can be conducted over a number of mechanisms. For context, cloud computing and big data may facilitate healthcare data, in electronic form, to grow larger and more ubiquitous. In part, the growth in data size and the improvement in data access may be facilitated by hardware improvements in speed and capacity of mass storage devices, as well as similar advances in processor and networking speed. Healthcare databases may be partitioned in large tables across a cluster of separate database servers with diverse storage technologies. For example, network-attached storage (NAS) and storage area networks (SANs) coupled with fast local area networks and Fiber Channel technology enable still larger, more loosely coupled configurations of databases and distributed computing power. Example implementations of distributed database storage may include X/Open XA standard and Oracle Real Application Clusters (RAC), both of which employs high-speed network connections between data storage servers. In the context of describing data storage technologies, server, system, and device may be used interchangeably.

For healthcare data in the age of cloud computing, the healthcare may be more likely managed by a host of different or heterogeneous database management systems. These database management systems may be hosted on servers spanning a wide region. Thus, a monolithic solution to rely on a traditional database management system to provide "cached" data to subsequent queries may not be realistic. Furthermore, even if a monolithic solution may be implemented for a particular application context, the solution may not provide the user universal access to a particular database engine and may impede portability of the solution. In contrast, a modularized solution can provide the aforementioned performance improvement without incurring the expense and the loss of portability of monolithic solutions. Nonetheless, the distinguishing characteristics of a layered or modularized solution as disclosed herein are far from obvious. In fact, the sheer complexity of implementing a distributed transaction with a modularized system is so daunting that no one has tackled such implementation.

Figure 2:
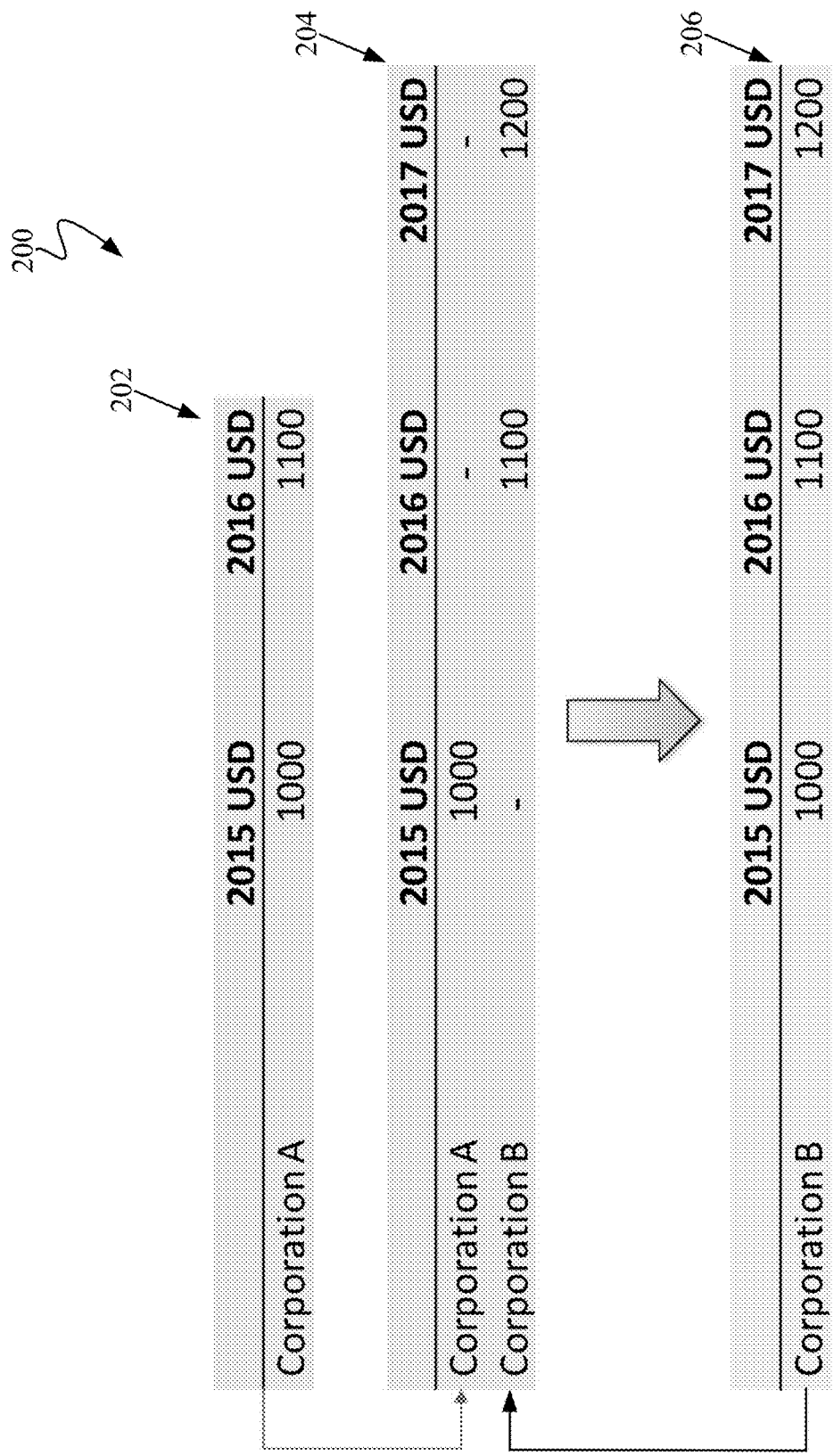
FIG. 2 illustrates an example of distributed databases with slowly changing dimensions.

Briefly referring to FIG. 2, an example 200 of apparent data gap is illustrated. In this illustration of example 200, data records from a first data server may contain data records 202 for corporation A that spans two years, namely, 2015 and 2016. When considering data records up to date, it would be advantageous to preserve historic time periods. After another year, the data warehouse will include already three years of data and the latest two years will be the fresh load, which is maintained at a second database as indicated by data record 204. In this illustration, there is a rename of a data item—Corporation A was renamed to Corporation B in the latest data supply. A naïve search would reveal the two columns of data records in the data warehouse as shown in FIG. 2. A gap in the data records becomes apparent when data records from Corporation B cannot be tracked back to the historic time periods. Some implementations disclosed herein enable the system to detect that data record labeled Corporation A and data record labeled Corporation B are effectively same data record despite the different labels. The implementations may subsequently merge these data records together using the latest label to generate a continuous record. Such improvement in the quality of the historic data can harvest more insight from data sources and render the resulting information more usable for client.

In the above context and returning to network configuration 100 of FIG. 1, data records at a second database may be accessed (112) when communication is established with the second database. The second database may be distinct and separate from the first database in terms of architecture or configuration. An analytic engine may reside at the primary data server that initiated communication with the first and second databases. The analytic engine may be receiving results from the first database and the second database. The analytic engine may be configured to determine whether a managed key is valid (113). For context, data records in the form of flat files (for example, csv or excel type files) may be received from diverse sources, rendering the recipient at the mercy of the mysterious updates in the source data. In the absence of managed keys, a determination on the interconnections of the data records can be difficult, if not impossible. For example, a mechanism may be in place to look for when a dimension value disappears in its entirety and another value appears with precisely the same associated sales. This likely points to either a modification to a description in the source data, a data correction assigning to a corrected dimension value, or a data entry error. The challenge is to consider the periodic data (number) restatements. While some data records may exhibit relatively straightforward changes, for example from "International Producer AAA Data" in the previous cycle (at a first database) to new "International Producer AAB Data," other data records may be less obvious when historical numbers get modified. It is therefore important to define some sensible rules by which to confirm that sales have "probably" moved from one record to another.

Some implementations may monitor changes within data records identified by unique combinations of the following four (4) dimensions, namely, panel, manufacturer, local product, and local pack description. These dimensions, in combination (not separately) may be considered the 'Primary Key' for the purpose of managing data records from diverse databases. In these implementations, managed keys to these dimension combinations (which are outside e.g. CORPORATION KEY) can be applied. Some implementations may generate a flat file (e.g., in the form of a csv file) that includes the descriptions for all dimension fields, and then these managed keys only (for example, when there is no manufacturer key). Additionally, a latest 'Master' file containing the distinct set of managed keys (along with the descriptions for the four dimensions) can be provided. The implementations may include multiple cycles of automation in which each cycle may look for instances where the data records for a unique combination may have moved (e.g., one or more of the dimension values has changed but the data records are otherwise similar enough to identify a candidate for 'Likely Change').

Referring to FIG. 3, a use case example 300 is illustrated for managing data records with four dimensions, namely, panel 302, manufacturer 304, local product 306, and local pack description 308. For each of the managed keys, some implementations may compare two data records' value for each individual time period over three years (e.g., 12 Qtrs or 36 Months). In this illustration, a 'Change To' candidate records ('New Record' in logs File) may be identified based on that record not being present in the previous cycle, but the record has data entries for at least two historical time periods. This rule may weed out most new launches. A 'Change From' candidate records ('Old Record' in the excel file) may be identified based on that record being present in the previous cycle but not the current cycle. Once changes are confirmed, an update to the description associated with the Managed Key may be triggered.

In more detail, some implementations may apply the following example of sequence of analysis to verify candidate records. First, if 75% of the time periods compared match exactly (i.e., a 100% match), and the remaining 25% are matched within a +/−2% variance, then a change is considered likely. The matching is determined based on a textual comparison month-by-month from all months over the time period. It can be more advantageous to avoid comparing the sum of data entries from all months because such summation can mask otherwise minutia month-by-month variations. Second, if data records, when individually compared, are within 0.5%+/− of each other for ALL the time periods, then a change is considered unlikely. Third, when candidate data records are compared during like time periods, a score may be assigned to each time period where the values are both non-zero and are within a cut-off threshold level of each other. For example, a score of 1 to each time period where the values are both non-zero and are within 5% of each other; and then matches with a score of 12 (for all 12 quarters) are declared positive. In this example, the remaining records with score of 11, or even lower, may be determined as positive, for example, when circumstances requiring less stringent match or pending human operator inspection. When a "Change From" candidate has more than one "Change To" candidate, neither may be considered as a likely change. In other words, the match may be discarded and both 'Change To' candidates may be handled as new records. Data records where all time periods in the last 3 years are 0 will be excluded from the above process for verifying a managed key. Data records with three or more lookup key changes which only have non-zero values for a single time period may also be excluded from the above process for verifying a managed key. These data records may still be assigned a managed key but they may be handled as new records because available information at the time remain insufficient to accurately link them to an existing managed key.

Further referring to FIG. 3, data records may be verified to be indexable by a management key when actual contents match even though only part of the entire dimensions match (e.g., only three of the four dimensions match). In one example, panel 302, manufacturer description 304, and local product 306 match while package description 308 differs. In this example, local pack description 308 may include different labels with "IVPB 4G/ML 24 100ML" (318) as "Change From" and "IVPB 4G/100 24 ML" as "Change To." In another example, manufacturer description 304 may include different labels with "Hospira" as "Change From" and "Pfizer" (314, 344) as "Change To." Items 314 and 344 both show "Change To" rows labelled as "Pfizer." This migration from a "Change From" row may be caused by, for example, corporate structure changes. Even though these data records do not have completely matching labels in the managed key that spans the four dimensions, the matching contents speak to the identical nature of the same data record. In both examples, implementations as disclosed can uncover the underlying matching contents before flagging the initial data record as "Change From" and the new data record as "Change To." In this manner, data records that otherwise remain separate may be merged by, for example, a join operation to form a contiguous record.

Similarly, in yet another example, candidate data records may include different labels under manufacturer description 304. As illustrated in FIG. 3, "Warner Chilcott" (324A) is a "Change From" label and "Teva Pharm. Belgium" (324C) is a "Change To" label. Subsequently, "Teva Pharm. Belgium" (324C) becomes a "Change From" label and "Vemedia Cons. Healt" (324B) is a "Change To" label. Thereafter, "Vemedia Cons. Healt" (324B) becomes a "Change From" label and "Teva Pharm. Belgium" (324C) resumes a "Change To" label. Even though these data records do not have completely matching labels in the managed key that spans the four dimensions, the matching contents speak to the identical nature of the same data record. As in the example of differing package description 308, data records that otherwise would be treated as separate entries can be identified as candidates for a join operation such that such candidates may be merged.

In still another example, candidate data records may include different and evolving labels under manufacturer description 304 as well as local pack description 308. As illustrated in FIG. 3, "CPR REV 50MG 10LO+H" (328) is a "Change From" label and "CPR REV 50/12. 5MG 10 LOSA" is a "Change To" label. Subsequently, "Pentafarma" (324C) is a "Change From" label and "Tecnigan" (334) is a "Change To" label. In a similar example, "Prostrakan" (354) is a "Change From" label and "Kyowa Kirin" is a "Change To" label. Subsequently, "PULV NAS 400Y DDS" is a "Change From" label and "PULV NAS 400Y DDS 1.55ML" (348) is a "Change To" label. In both example, these are labels of separate dimensions. Even though these data records do not have completely matching labels in the managed key that spans the four dimensions, the matching contents speak to the identical nature of the same data record. Implementations disclosed herein may track the migrating nature of slowly changing dimensions such that data records with evolving labels may be identified and joined.

Returning to FIG. 1, in response to determining that a managed key is valid with respect to candidate data records (114), some implementations may reconcile the data records by merging the candidate data records (115). In some implementations, the combined data record may include a contiguous segment that spans the continuous time period covered by data records from separate data servers. For example, data records with evolving labels from different sources that cover an overlapping period of time can be identified for a merge. The resulting entries may be provided in the merged database 117. The database management system may also adjust the "Change From" label to "Change To" label in merged database 117 as well as separate data servers. In this example, the determination of whether a managed key is valid may incorporate fuzzy logic to probabilistically evaluate the extent of matching contents based on context.

In response to determining that a managed key is invalid with respect to candidate data records (114), some implementations may reconcile the data records by combining the candidate data records as separate records (116). In some implementations, the combined data record may include the add-on data record as new data record. The resulting entries may be provided in the updated database 118. The database management system may keep the labels of the dimensions unchanged.

Figure 4:
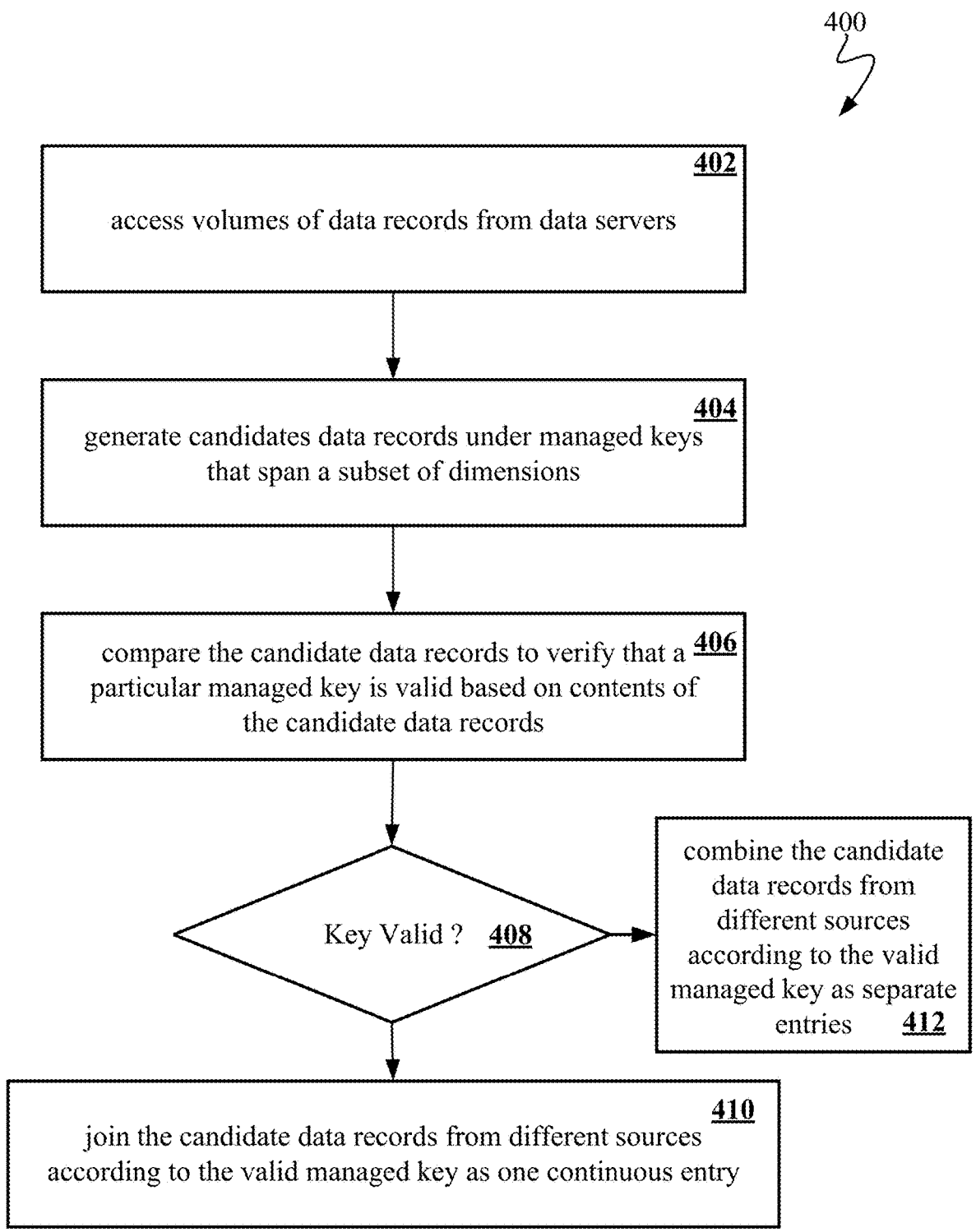
FIG. 4 shows an example of a process for handling distributed databases with slowly changing dimensions.

FIG. 4 illustrates an example of a flow chart 400 for implementing the disclosed process. Initially, volumes of data records may be received (402). The volumes of data may be arranged in, for example, csv format with common delimiters. In this example, the various columns may form the respective dimensions. The volumes of data records may arrive from diverse databases that each may have its own convention of labeling the various dimensions.

In this illustration, candidate data records may be identified from the diverse sources by using managed keys to index such data records (404). As discussed, the managed keys span multiple dimensions, which can be used to index specific matching data records.

Subsequently, the candidate data records may be compared based on the actual contents of the candidate data records keyed by a particular managed key (406). Because the managed keys include slowly changing dimensions (SCDs), various implementations may incorporate different matching criterion, depending on the criticality of the match and the estimated turn-around time. In one example, the match may be premised on identical matches from the majority of the data contents. In another example, the match may be determined based on a similarity score that quantifies, for each time quanta, the degree of similarity between the candidate data records.

In response to determining that the managed key is valid by virtue of a match (408), the candidate data records may be merged as one continuous entry (410). Implementations may additionally relabel the impacted dimensions to render the updated label consist and current. Here, the determination may incorporate fuzzy logic that involves, for example, a probabilistic readout to gauge the extent of matching contents based on context. In response to determining that the managed key is invalid by virtue of a mismatch (408), the candidate data records may be combined as separate entries (412) that span, for example, multiple rows.

While the comparison may introduce risk of false positive records, this risk is mitigated by reports that provide transparence on the merged records and any exceptions should be handled as custom rules that will be applied afterwards. Indeed, implementations may incorporate deep learning mechanisms to have the rules of matching refined based on operator feedback based on the report file.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:
obtaining data records from a first volume and data records from a second volume, wherein each of the data records is keyed by a respective key,
   wherein each key spans a subset of dimensions, wherein each of the dimensions indicates a respective attribute of the data records,
   wherein at least one dimension from the subset of dimensions is labelled differently between the first volume and the second volume,
determining that a particular key is invalid based on a comparison of the data records from the first volume with the data records from the second volume, wherein the data records from the first volume and the data records from the second volume cover an overlapping period of time; and
combining the data records from the first volume with the data records from the second volume according to the invalid key such that the data records from the first volume and the data records from the second volume keyed by the invalid key are accessible as a single entry.

2. The method of claim 1, wherein the comparison of the data records from the first volume with the data records from the second volume comprises:
comparing contents of the data records from the first volume with the contents of the data records from the second volume.

3. The method of claim 2, wherein the data records from the first volume and the data records from the second volumes cover more than a threshold duration within the overlapping period.

4. The method of claim 2, wherein the comparison of the data records from the first volume with the data records from the second volume utilizes a fuzzy logic.

5. The method of claim 4, wherein the fuzzy logic comprises:
determining that the contents of the data records from the first volume and the data records from the second volume do not substantially match, wherein the at least one dimension is labelled differently.

6. The method of claim 5, wherein the contents of the data records from the first volume and the contents of the data records from the second volume do not substantially match when the data records from the first volume and the data records from the second volume are identical for no more than a threshold percentage of a duration within the overlapping period.

7. The method of claim 5, wherein the contents of the data records from the first volume and the contents of the data records from second volume do not substantially match when the data records from the first volume and the data records from the second volume are textually no more than a threshold percent identical.

8. The method of claim 5, further comprising:
scoring a similarity between the contents of the data records from the first volume with the contents of the data records from the second volume, wherein the contents of the data records from the first volume and the contents of the data records from the second volume do not substantially match when the scored similarity does not exceed a threshold value.

9. The method of claim 1, wherein the subset of dimensions includes three or more dimensions.

10. A computer system comprising one or more processors that are configured to perform operations of:
obtaining data records from a first volume and data records from a second volume, wherein each of the data records is keyed by a respective key,
   wherein each key spans a subset of dimensions, wherein each of the dimensions indicates a respective attribute of the data records,
   wherein at least one dimension from the subset of dimensions is labelled differently between the first volume and the second volume,
determining that a particular key is invalid based on a comparison of the data records from the first volume with the data records from the second volume, wherein the data records from the first volume and the data records from the second volume cover an overlapping period of time; and
combining the data records from the first volume with the data records from the second volume according to the invalid key such that the data records from the first volume and the data records from the second volume keyed by the invalid key are accessible as a single entry.

11. The computer system of claim 10, wherein the comparison of the data records from the first volume with the data records from the second volume comprises:
comparing contents of the data records from the first volume with the contents of the data records from the second volume.

12. The computer system of claim 11, wherein the data records from the first volume and the data records from the second volumes cover more than a threshold duration within the overlapping period.

13. The computer system of claim 11, wherein the comparison of the data records from the first volume with the data records from the second volume utilizes a fuzzy logic.

14. The computer system of claim 13, wherein the fuzzy logic comprises:
determining that the contents of the data records from the first volume and the data records from the second volume do not substantially match, wherein the at least one dimension is labelled differently.

15. The computer system of claim 14, wherein the contents of the data records from the first volume and the contents of the data records from the second volume do not substantially match when the data records from the first volume and the data records from the second volume are identical for no more than a threshold percentage of a duration within the overlapping period.

16. The computer system of claim 14, wherein the contents of the data records from the first volume and the contents of the data records from second volume do not substantially match when the data records from the first volume and the data records from the second volume are textually no more than a threshold percent identical.

17. The computer system of claim 14, wherein the operations further comprise:
scoring a similarity between the contents of the data records from the first volume with the contents of the data records from the second volume, wherein the contents of the data records from the first volume and the contents of the data records from the second volume do not substantially match when the scored similarity does not exceed a threshold value.

18. The computer system of claim 10, wherein the subset of dimensions includes three or more dimensions.

* * * * *